(12) United States Patent
Liang et al.

(10) Patent No.: US 8,987,466 B2
(45) Date of Patent: Mar. 24, 2015

(54) SILICON-CONTAINING BIANTHRACENE DERIVATIVE, PRODUCTION PROCESS AND USE THEREOF, AND ORGANIC ELECTROLUMINESCENT DEVICE

(71) Applicants: BOE Technology Group Co., Ltd., Beijing (CN); JiLin OLED Material Tech. Co., Ltd., Changchun (CN)

(72) Inventors: Yinan Liang, Beijing (CN); Xiaoyu Ma, Beijing (CN); Hui Wang, Beijing (CN); Wenyu Ma, Beijing (CN)

(73) Assignees: BOE Technology Group Co., Ltd., Beijing (CN); JiLin OLED Material Tech. Co., Ltd., Changchun (CN)

( * ) Notice: Subject to any disclaimer, the term of this patent is extended or adjusted under 35 U.S.C. 154(b) by 0 days.

(21) Appl. No.: 14/164,668

(22) Filed: Jan. 27, 2014

(65) Prior Publication Data

US 2014/0343291 A1    Nov. 20, 2014

(30) Foreign Application Priority Data

May 15, 2013 (CN) .......................... 2013 1 0180037

(51) Int. Cl.
*C07F 7/08* (2006.01)
*C07F 7/10* (2006.01)
*H01L 51/00* (2006.01)

(52) U.S. Cl.
CPC .......... *C07F 7/0809* (2013.01); *H01L 51/0094* (2013.01); *C07F 7/0812* (2013.01)
USPC ........................................................ 548/110

(58) Field of Classification Search
CPC .. C07F 7/0809; C07F 7/0812; H01L 51/0094
See application file for complete search history.

(56) References Cited

FOREIGN PATENT DOCUMENTS

| CN | 101130553 A | 2/2008 | |
|----|-------------|--------|---|
| CN | 101730731 A | 6/2010 | |
| CN | 102031104 A | 4/2011 | |
| JP | 2003-138251 | * 5/2003 | ............. C09K 11/06 |

OTHER PUBLICATIONS

First Office Action for Chinese Patent Application No. 201310180037.2, dated Dec. 16, 2014, 15 pages.

\* cited by examiner

*Primary Examiner* — Joseph Kosack
(74) *Attorney, Agent, or Firm* — Westman, Champlin & Koehler, P.A.

(57) ABSTRACT

The invention provides a silicon-containing bianthracene derivative, a production process and use thereof, and an organic electroluminescent device. The invention belongs to the technical field of organic electroluminescence, and can give a blue light-emitting material being able to form a dense film. The silicon-containing bianthracene derivative has a molecular structure of the following general formula, wherein R group represents an aryl group having a carbon atom number of 6-14, an aromatic heterocyclic group having a carbon atom number of 8-18, a fused-ring aromatic group having a carbon atom number of 9-15, a fluorenyl group, or a triarylamino group. The silicon-containing bianthracene derivative mentioned in the invention can be used in an organic electroluminescent device.

15 Claims, 2 Drawing Sheets

SILICON-CONTAINING BIANTHRACENE DERIVATIVE, PRODUCTION PROCESS AND USE THEREOF, AND ORGANIC ELECTROLUMINESCENT DEVICE

CROSS-REFERENCE TO RELATED APPLICATION

This Application is a non-provisional Application of Chinese Application No. CN 201310180037.2, filed May 15, 2013, in Chinese, the contents of which are hereby incorporated by reference in their entirety.

FIELD OF THE INVENTION

The invention relates to the technical field of organic electroluminescence, particularly, to a silicon-containing bianthracene derivate, a production process and use thereof, and an organic electroluminescent device.

BACKGROUND OF THE INVENTION

Since reported by C. W. Tang, et al in 1987, the organic light-emitting diode (Organic Light-Emitting Device, OLED) has been developed rapidly. The potential uses thereof are for full color flat panel display and for white light-emitting solid-state illumination. The selection of luminescent materials is of significant importance for an organic electroluminescent device such as an OLED. In order to realize the full color flat panel display, a material, which emits one of the three primary colors (i.e. red, green and blue) and has high color purity and high efficiency, is a necessary precondition.

Reported blue light-emitting materials mainly include aromatic hydrocarbons, arylamines, organoborons, organosilicons, and the like. The aromatic hydrocarbons are materials emitting blue light, which have been researched more, and include fluorenes, styrenes, anthracenes, and the like. Among these, anthracene-based derivates have the advantages such as high fluorescence quantum efficiency and good stability. However, the organic electroluminescent thin film made thereof has a problem that the film-forming is unstable, which accelerates the deterioration of the device and influences the life of the device. Due to the non-planar structure thereof, bianthracene-based compounds greatly improve the problem of poor film-forming, but such materials cannot provide a dense film. When they are used to prepare thin films, generally, a phenomenon, that the surface of the crystal is rough or has pinholes, will occur, which further results in leakage of current or catastrophic device failure.

SUMMARY OF THE INVENTION

In order to obtain a blue light-emitting material being able to form a dense film, the invention provides a silicon-containing bianthracene derivate, a production process and use thereof, and an organic electroluminescent device.

In order to achieve the object mentioned above, the invention adopts the following technical solutions.

A silicon-containing bianthracene derivate having a molecular structure of the following general formula:

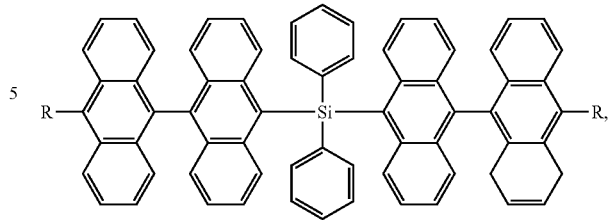

wherein R group represents an aryl group having a carbon atom number of 6-14, an aromatic heterocyclic group having a carbon atom number of 8-18, a fused-ring aromatic group having a carbon atom number of 9-15, a fluorenyl group, or a triarylamino group.

Optionally, the R group is one selected from N-phenyl-3-carbazyl, triphenylamino, 2-anthranyl, 2-phenanthryl, 2-naphthyl and 9,9-dimethyl-2-fluorenyl.

A production process for the silicon-containing bianthracene derivate provided by the invention, comprising the following steps of Step S1: adding bis[10-(9-bromoanthranyl)]diphenyl silane and an anthranyl boronic acid para-substituted by the R group into a reaction vessel;

Step S2: adding potassium carbonate and a solvent;

Step S3: adding a catalyst;

Step S4: raising the reaction temperature and performing refluxing, performing a reaction sufficiently to obtain the silicon-containing bianthracene derivate.

Optionally, the bis[10-(9-bromoanthranyl)]diphenyl silane in Step S1 is prepared from 9,10-dibromoanthracene and diphenyl dichlorosilane.

Optionally, the production process for the bis[10-(9-bromoanthranyl)]diphenyl silane in the Step S1 comprises the following Steps of:

Step N1: adding 9,10-dibromoanthracene as a reactant to anhydrous tetrahydrofuran as a solvent;

Step N2: adding a solution of n-butyl lithium dropwise;

Step N3: stirring at room temperature, and cooling;

Step N4: adding diphenyl dichlorosilane, performing heating gradually to room temperature, stirring and cooling;

Step N5: obtaining the bis[10-(9-bromoanthranyl)]diphenyl silane, which can be directly used in Step S1, through extraction, washing, drying overnight, purification by column chromatography, and recrystallization.

Optionally, n-butyl lithium and 9,10-dibromoanthracene in the Step N2 have the following parts by mole of:
n-butyl lithium: 1-1.2 parts;
9,10-dibromoanthracene: 1 part.

Optionally, diphenyl dichlorosilane and 9,10-dibromoanthracene in the Step N4 have the following parts by mole of:
diphenyl dichlorosilane: 1 part;
9,10-dibromoanthracene: 3-4 parts.

Optionally, the solvent in the purification by column chromatography in the Step N5 is a mixed solvent of n-hexane and chloroform at a volume ratio of 1:4.

Optionally, bis[10-(9-bromoanthranyl)]diphenyl silane and the anthranyl boronic acid para-substituted by the R group in the Step S1 respectively have the following parts by mole of:
bis[10-(9-bromoanthranyl)]diphenyl silane: 1 part;
the anthranyl boronic acid para-substituted by the R group: 2.5-3 parts.

Optionally, potassium carbonate and bis[10-(9-bromoanthranyl)]diphenyl silane in the Step S2 respectively have the following parts by mole of:

potassium carbonate: 3-4 parts;
bis[10-(9-bromoanthranyl)]diphenyl silane: 1 part.
Optionally, the solvent in the Step S2 is a mixed solvent of tetrahydrofuran and water at a volume ratio of 2:1.
Optionally, the catalyst and bis[10-(9-bromoanthranyl)] diphenyl silane in the Step S3 have the following parts by mole of:
the catalyst: 1 part;
bis[10-(9-bromoanthranyl)]diphenyl silane: 50-100 parts.
Preferably, in the Step S4, the reaction temperature is 70-80° C., and the reflux reaction time is 24-30 hours.
Use of the silicon-containing bianthracene derivate provided by the invention in an organic electroluminescent device, wherein the silicon-containing bianthracene derivate is used as an organic luminescent material, a luminescent host material, or a transporting material in the organic electroluminescent device.
An organic electroluminescent device comprising the silicon-containing bianthracene derivate provided by the invention as an organic luminescent material, a luminescent host material, or a transporting material.
The invention provides a silicon-containing bianthracene derivate, a production process and use thereof, and an organic electroluminescent device. The silicon-containing bianthracene derivate has a silicon atom as the center, contains anthranyl and a non-planar structure, wherein the strong electron withdrawing groups R are introduced by symmetrical substitution and a high-level π-conjugated system is formed, which has better ability for accepting electron. At the same time, in the design of the molecule, the chemical structure of the silicon-containing bianthracene derivate is symmetric, and the R groups are introduced symmetrically, which enlarges the non-planar structure and thus provides a dense steric hindrance, allowing it to form an even, dense film layer during film-forming, and effectively preventing the molecule of silicon-containing bianthracene derivate from forming an agglomerated solid state or a film layer not uniform and continuous enough during film-forming, so as to make the formed dense film more even and more smooth. Additionally, by means of various transformations of the symmetrically substituted R groups, it also possible to modify the structure thereof, to adjust the luminous property of the silicon-containing bianthracene derivate effectively. The luminescent device made from the silicon-containing bianthracene derivate as a raw material has higher luminescence efficiency and more stable performance, which allows it more suitable to be used in the field of electroluminescence.

DETAILED DESCRIPTION OF THE INVENTION

Figure 1:
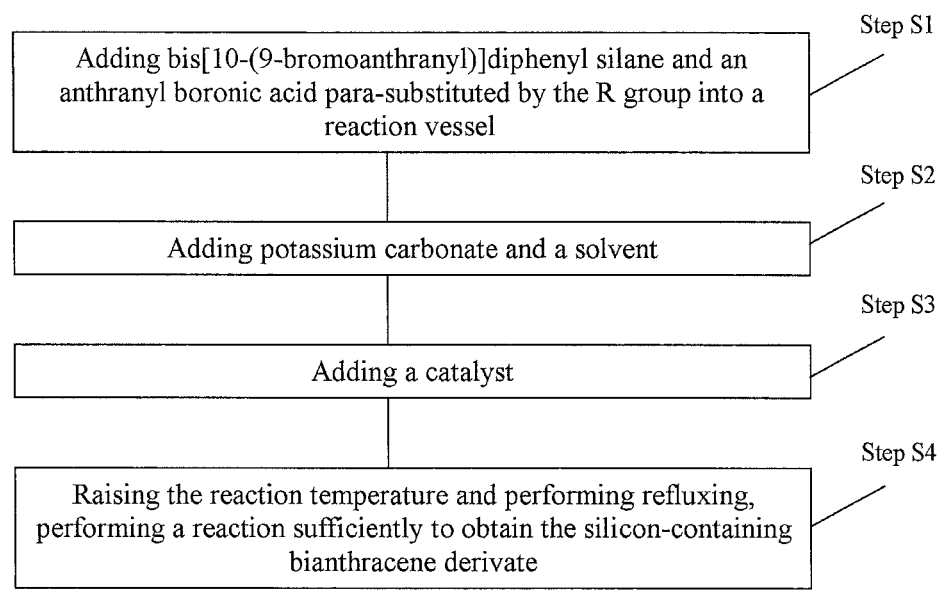
FIG. 1 is a flow chart of the production process for the silicon-containing bianthracene derivate provided by the invention.
Figure 2:
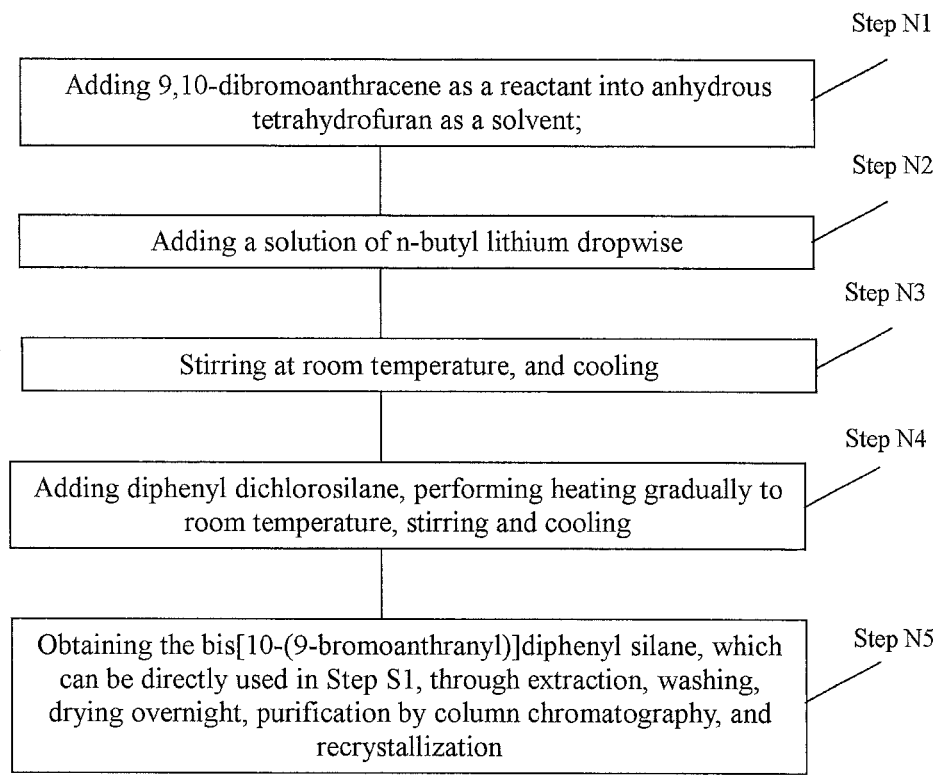
FIG. 2 is a flow chart of the production process for bis[10-(9-bromoanthranyl)]diphenyl silane provided by the invention.

The technical solutions in the invention are described clearly and fully below by referring to the drawings in the invention. Obviously, the examples described herein are only a part of the examples of the invention, but not all of them. All other examples, which are obtained by those skilled in the art on the basis of the examples in the invention on the premise that they do not pay an inventive labour, belong to the protection scope of the invention.

The silicon-containing bianthracene derivate, the production process and use thereof, and the organic electroluminescent device according to the invention are described in detail below by referring to the drawings.

The invention provides a silicon-containing bianthracene derivate having a molecular structure of the following general formula:

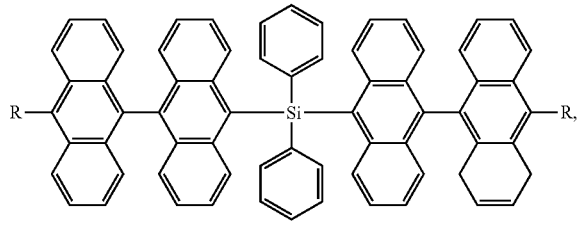

wherein R group represents an aryl group having a carbon atom number of 6-14, an aromatic heterocyclic group having a carbon atom number of 8-18, a fused-ring aromatic group having a carbon atom number of 9-15, a fluorenyl group, or a triarylamino group.

The R group mentioned above belongs to aromatic compounds, has a π-conjugated plane and is a strong electron withdrawing group. The R group is combined with the silicon-containing bianthracene derivate to form a larger π conjugated plane, which has better ability for accepting electron. The silicon-containing bianthracene derivate has a symmetrical structure, and R groups are introduced at both ends of the molecule, which enlarges the non-planar structure of the molecule and thus provides a dense steric hindrance.

The invention provides a silicon-containing bianthracene derivate, which has a silicon atom as the center, contains anthranyl and a non-planar structure, wherein the strong electron withdrawing groups R are introduced by symmetrical substitution and a high-level π-conjugated system is formed, which has better ability for accepting electron. At the same time, in the design of the molecule, the chemical structure of the silicon-containing bianthracene derivate is symmetric, and the R groups are introduced symmetrically, which enlarges the non-planar structure and thus provides a dense steric hindrance, effectively preventing the molecule of silicon-containing bianthracene derivate from forming an agglomerated solid state or a film layer not uniform and continuous enough during film-forming, so as to make the formed dense film more even and more smooth. Additionally, by means of various tranformations of the symmetrically substituted R groups, it also possible to modify the structure thereof, to adjust the luminous property of the silicon-containing bianthracene derivate effectively, and to obtain a blue light-emitting material having better luminous property. The luminescent device made from the silicon-containing bianthracene derivate as a raw material has higher luminescence efficiency and more stable performance, which allows it more suitable to be used in the field of electroluminescence.

Optionally, in other embodiments of the invention, the R group is one selected from N-phenyl-3-carbazyl, triphenylamino, 2-anthranyl, 2-phenanthryl, 2-naphthyl and 9,9-dimethyl-2-fluorenyl. Here, the silicon-containing bianthracene derivates having an above-mentioned R group are represented in order by the following molecular structural formulae 001, 002, 003, 004, 005, and 006.

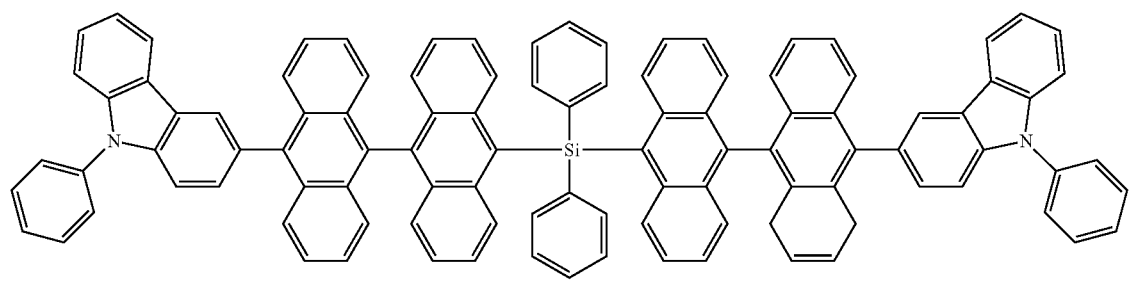
001
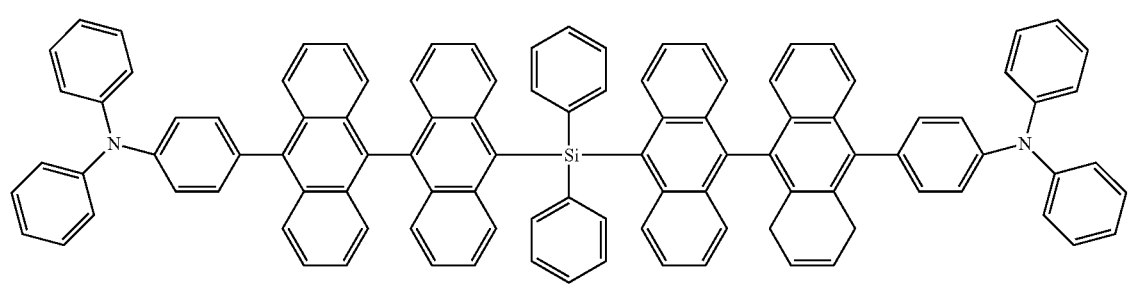
002
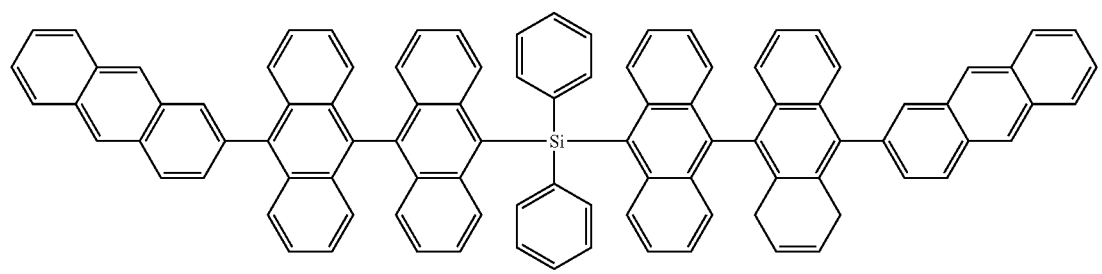
003
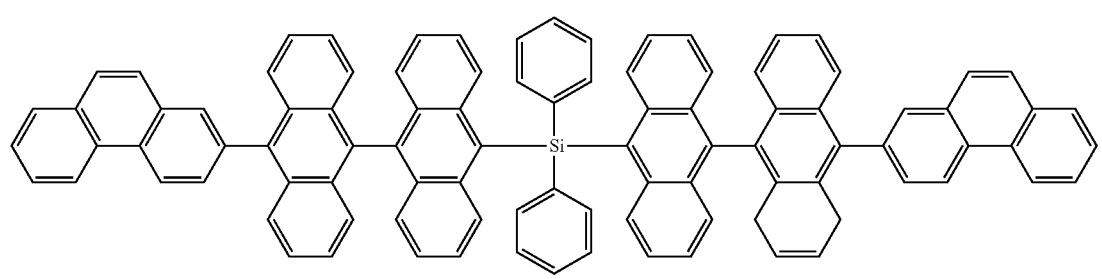
004
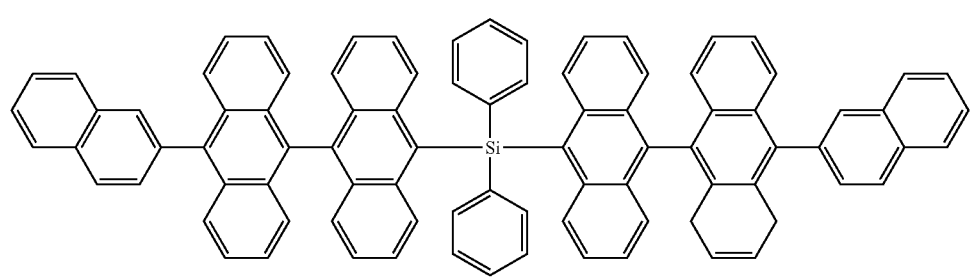
005

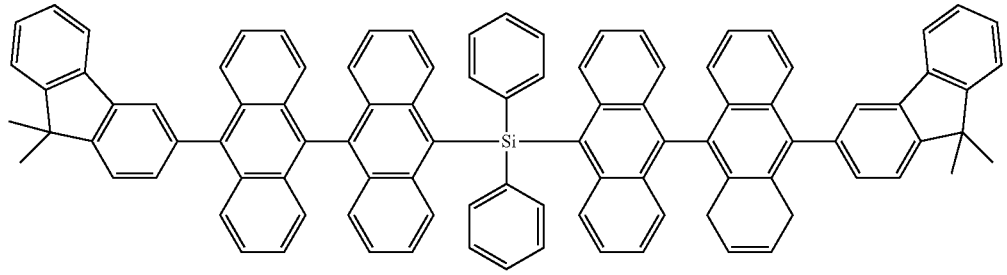

Corresponding to the above-mentioned silicon-containing bianthracene derivate, the invention further provides a production process for the silicon-containing bianthracene derivate. The reaction principle of the present process is Suzuki coupling reaction. Specifically, the process comprises the following steps of:

Step S1: adding bis[10-(9-bromoanthranyl)]diphenyl silane and an anthranyl boronic acid para-substituted by the R group into a reaction vessel.

In this step, an appropriate amount of reactants, i.e. bis[10-(9-bromoanthranyl)]diphenyl silane and an anthranyl boronic acid para-substituted by the R group, are weighed in a reaction vessel. Preferably, bis[10-(9-bromoanthranyl)]diphenyl silane and the anthranyl boronic acid para-substituted by the R group selected in this step have the following parts by mole of: bis[10-(9-bromoanthranyl)]diphenyl silane: 1 part; the anthranyl boronic acid para-substituted by the R group: 2.5-3 parts. It can be appreciated that the invention is not limited thereto and those skilled in the art can determine the parts by mole of the above-mentioned reactants and solvent according to the disclosure of the invention and the well-known general knowledge or the conventional technical means in the art.

It is should be indicated that in the present production process, all of the reactants, as well as the reactants, the solvent or the catalyst in the sequent steps are added under a condition of nitrogen protection. Firstly, people can evacuate the reaction environment, charge nitrogen gas, and add the reactants under nitrogen protection, so that the interference in the reaction from the oxygen in the reaction vessel is avoided. Secondly, the reactants, the solvent or the catalyst in the sequent steps are further added in the condition that nitrogen is kept charging, so that any stage in the operation is carried out in a nitrogen environment.

It can be appreciated that the process of nitrogen protection can also comprise performing the corresponding nitrogen protection after the addition of the reactants in Step S1, so as to ensure that the reactants, the solvent or the catalyst in the sequent steps are added under the nitrogen protection.

The invention is not limited thereto, and those skilled in the art can select other gases, which do not interfere in the reaction, according to the disclosure of the invention and the well-known general knowledge or the conventional technical means in the art.

Step S2: adding potassium carbonate and a solvent.

In this step, potassium carbonate and a solvent are weighed in appropriate amount. Optionally, potassium carbonate and bis[10-(9-bromoanthranyl)]diphenyl silane selected in this step respectively have the following parts by mole of: potassium carbonate 3-4 parts; bis[10-(9-bromoanthranyl)]diphenyl silane: 1 part. Preferably, potassium carbonate and bis[10-(9-bromoanthranyl)]diphenyl silane selected in this step respectively have the following parts by mole of: potassium carbonate 3 parts; bis[10-(9-bromoanthranyl)]diphenyl silane: 1 part.

Optionally, the solvent in the present step is a mixed solvent of tetrahydrofuran and water, further preferably, a mixed solvent of tetrahydrofuran and water at a volume ratio of 2:1. It can be appreciated that the invention is not limited thereto and those skilled in the art can determine the parts by mole of the above-mentioned reactants and solvent according to the disclosure of the invention and the well-known general knowledge or the conventional technical means in the art.

Step S3: adding a catalyst.

Optionally, the catalyst in the present step can be tetrakis (triphenylphosphine) palladium. Further preferably, the catalyst and bis[10-(9-bromoanthranyl)]diphenyl silane have the following parts by mole of: the catalyst: 1 part; bis[10-(9-bromoanthranyl)]diphenyl silane: 50-100 parts. It can be appreciated that the above mentioned is merely an illustrated description and those skilled in the art can also select other catalysts suitable for the Suzuki coupling reaction and determine the corresponding amount to be used.

Step S4: raising the reaction temperature and performing refluxing, performing a reaction sufficiently to obtain the silicon-containing bianthracene derivate. Preferably, in the Step S4, the reaction temperature is 70-80° C., and the reflux reaction time is 24-30 hours.

It is should be indicated that the reaction product obtained in the present step is a crude product, which can be subjected to a further purification step, if necessary. Optionally, the purification steps include operations such as cooling, precipitation, vacuum filtration, washing the resultant filter cake with water, ethanol and diethyl ether, and then performing purification by column chromatography or the like, and thus a reaction product having higher purity can be obtained. Here, the solvent used in the purification by column chromatography is preferably a mixed solvent of dichloromethane and petroleum ether at a volume ratio of 3:1.

The invention provides a production process for a silicon-containing bianthracene derivate. The production process introduces the strong electron withdrawing group R symmetrically to a silicon-containing bianthracene derivate, to make it have better ability for accepting electron and thus have very high luminescence efficiency. At the same time, the introduction of the R groups also makes the silicon-containing bianthracene derivate more dense in terms of steric hindrance, and allows it to form an even, smooth, and dense film so as to prepare a blue light-emitting material having stable performance. In this process, the synthesis steps are simple, the cost of the solvents to be used is lower, and the resultant derivate has high purity, and the yield can be 88% or more, which can meet the requirement of large scale industrialization.

In other embodiments of the invention, bis[10-(9-bromoanthranyl)]diphenyl silane in the Step S1 is prepared from 9,10-dibromoanthracene and diphenyl dichlorosilane. Optionally, the production process thereof specifically comprises the following steps of:

Step N1: adding 9,10-dibromoanthracene as a reactant to anhydrous tetrahydrofuran as a solvent;

Step N2: adding a solution of n-butyl lithium dropwise;

Optionally, n-butyl lithium and 9,10-dibromoanthracene in the Step N2 have the following parts by mole of: n-butyl lithium: 1-1.2 parts; 9,10-dibromoanthracene: 1 part.

Step N3: stirring at room temperature, and cooling;

Step N4: adding diphenyl dichlorosilane, performing heating gradually to room temperature, stirring and cooling;

Optionally, diphenyl dichlorosilane and 9,10-dibromoanthracene in the Step N4 have the following parts by mole of: diphenyl dichlorosilane: 1 part; 9,10-dibromoanthracene: 3-4 parts.

Step N5: obtaining the bis[10-(9-bromoanthranyl)]diphenyl silane, which can be directly used in Step S1, through extraction, washing, drying overnight, purification by column chromatography, and recrystallization.

Optionally, the solvent in the purification by column chromatography in the Step N5 is a mixed solvent of n-hexane and chloroform at a volume ratio of 1:4.

It can be appreciated that the Steps N1-N5 are merely a preferred way for synthesizing bis[10-(9-bromoanthranyl)]diphenyl silane by using 9,10-dibromoanthracene and diphenyl dichlorosilane in the invention. The invention is not limited thereto and those skilled in the art can select a specific way to synthesize bis[10-(9-bromoanthranyl)]diphenyl silane according to the disclosure of the invention and the well-known general knowledge or the conventional technical means in the art.

Corresponding to the above-mentioned silicon-containing bianthracene derivate, the invention also provides the use of the above-mentioned silicon-containing bianthracene derivate in an organic electroluminescent device. The silicon-containing bianthracene derivate is used as an organic luminescent material, a luminescent host material, or a transporting material in the organic electroluminescent device.

This kind of silicon-containing bianthracene derivate provided by the invention can be used as an electroluminescent material, a luminescent host material or a transporting material in an organic electroluminescent device. The introduction of the R groups makes the silicon-containing bianthracene derivate more dense in terms of steric hindrance, and allows it to form an even and smooth dense film. Occurrence of the phenomenon, that the surface of the crystal is rough or has pinholes, is prevented effectively, so that the blue light-lighting device prepared therefrom is more stable in terms of performance and can be used in an organic electroluminescent device better. Additionally, the introduction of the R groups causes that the silicon-containing bianthracene derivate has a better ability for accepting electron and thus has a very high luminescence efficiency, which further improves the quality of the luminescence of the organic electroluminescent device.

Corresponding to the above-mentioned silicon-containing bianthracene derivate, the invention also provides an organic electroluminescent device. The organic electroluminescent device comprises the silicon-containing bianthracene derivate as a luminescent material, a luminescent host material, or a transporting material.

When a blue light-emitting device is prepared by using the silicon-containing bianthracene derivate provided by the invention as a blue light-emitting material, the introduction of the R groups makes the silicon-containing bianthracene derivate more dense in terms of steric hindrance, and allows it to form an even and smooth dense film. Occurrence of the phenomenon, that the surface of the crystal is rough or has pinholes, is prevented effectively, so that the blue light-lighting device prepared therefrom is more stable in terms of performance and can be used in an organic electroluminescent device better. Additionally, the introduction of the R groups causes that the silicon-containing bianthracene derivate has a better ability for accepting electron and thus has a very high luminescence efficiency, which further improves the quality of the luminescence of the organic electroluminescent device.

In order to describe the silicon-containing bianthracene derivate, the production process and use thereof, and the organic electroluminescent device provided by the invention, the detailed description is performed below by referring to specific Examples. Examples 1-6 describes the synthesis processes and tests for performance of the silicon-containing bianthracene derivates of the previous molecular structural formulae 001-006 in detail.

Synthesis of an intermediate, that is, bis[10-(9-bromoanthranyl)]diphenyl silane:

200 ml anhydrous tetrahydrofuran and 9,10-dibromoanthracene (199.1 g, 592.5 mmol) were added into a three-necked flask equipped with a heating means, a refluxing means and a stirring means at a temperature of −78° C. Then n-butyl lithium (0.37 g, 592.0 mmol) was added dropwise slowly. After the addition was completed, the mixture was stirred for 3 hours at room temperature. The reactants after the agitation were cooled to −78° C. Thereafter, diphenyl dichlorosilane was added, heated to room temperature, and stirred for 15 hours. After being stirred to homogenization, the reaction mixture was cooled to −80° C.--75° C., After extracted with diethyl ether and water for 3 times sequentially and washed with aqueous salt solution twice, it was dried over magnesium sulfate overnight. On the next day, after the solvent was evaporated and dried, the crude product was purified by column chromatography (n-hexane/chloroform=1:4) and recrystallized by using a mixed solvent of chloroform and methanol so as to obtain the bis[10-(9-bromoanthranyl)]diphenyl silane, which could be directly used in Examples 1-6 below.

Example 1

Synthesis of Compound 001-Silicon-Containing Bianthracene Derivate Containing N-penhylcarbazyl Under a nitrogen environment, bis[10-(9-bromoanthranyl)]diphenyl silane (34.73 g, 50 mmol) and 10-(N-penhylcarbazyl)-9-anthranyl boronic acid (57.92 g, 125 mmol) were added into a three-necked flask equipped with a heating means, a refluxing means and a stirring means. Then potassium carbonate (13.82 g, 100 mmol), tetrahydrofuran (250 ml) and water (125 ml) were added. Thereafter, tetrakis(triphenylphosphine) palladium (0.58 g, 0.5 mmol) was added. The temperature was raised to 70° C., and the mixture was reacted for 24 hours while refluxing. The resultant mixture was cooled to room temperature, and after a solid was precipitated, vacuum filtration was carried out. After the resultant filter cake was washed with water, ethanol and diethyl ether in this order, it was purified by column chromatography (dichloromethane:petroleum ether=3:1). The solvent was recovered. After drying, an off-white Compound 001 (61.04 g) was obtained, and the yield thereof was 89% or more.

The specific synthesis route for Compound 001 was as follows:

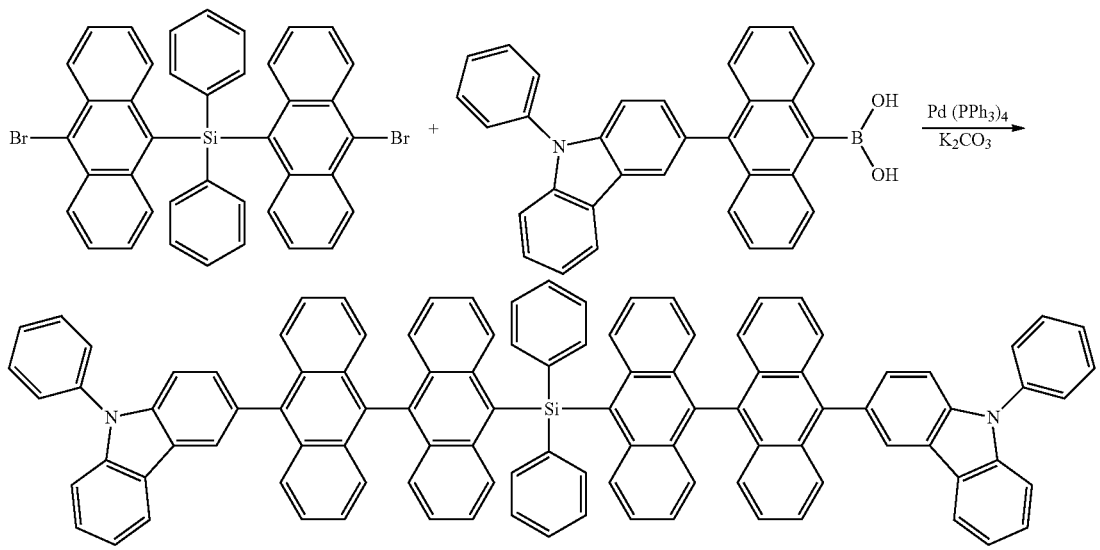

As the result of the analysis for Compound 001 by mass spectrography, the measured value of the molecular weight of the compound was 1371.72, while the calculated one was 1371.74.

As the result of the analysis for Compound 001 by an elemental analyzer, the measured values of each element in the compound were C, 91.05%; H, 4.86%; N, 2.03%; Si, 2.06%; while the calculated ones were C, 91.06%; H, 4.85%; N, 2.04%, Si, 2.05%.

Example 2

Synthesis of Compound 002-Silicon-Containing Bianthracene Derivate Containing Triphenylamino Under a nitrogen environment, bis[10-(9-bromoanthranyl)]diphenyl silane (34.73 g, 50 mmol) and 10-(triphenylamino)-9-anthranyl boronic acid (60.50 g, 130 mmol) were added into a three-necked flask equipped with a heating means, a refluxing means and a stirring means. Then potassium carbonate (15.89 g, 115 mmol), tetrahydrofuran (250 ml) and water (125 ml) were added. Thereafter, tetrakis(triphenylphosphine) palladium (0.69 g, 0.6 mmol) was added. The temperature was raised to 72° C., and the mixture was reacted for 25 hours while refluxing. The resultant mixture was cooled to room temperature, and after a solid was precipitated, vacuum filtration was carried out. After the resultant filter cake was washed with water, ethanol and diethyl ether in this order, it was purified by column chromatography (dichloromethane:petroleum ether=3:1). The solvent was recovered. After drying, an off-white Compound 002 (61.91 g) was obtained, and the yield thereof was 90% or more.

The specific synthesis route for Compound 002 was as follows:

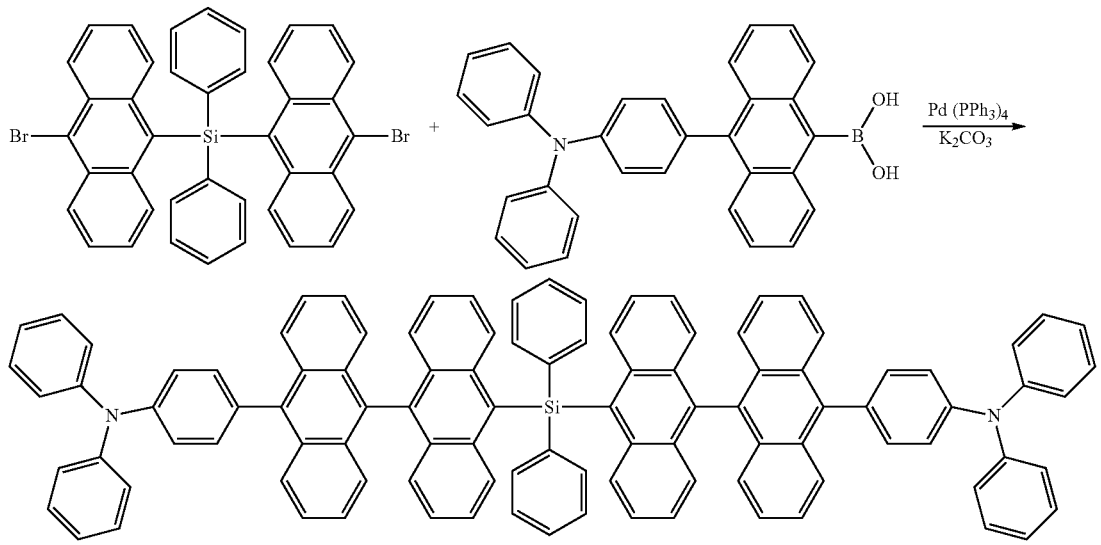

As the result of the analysis for Compound 002 by mass spectrography, the measured value of the molecular weight of the compound was 1375.79, while the calculated one was 1375.77.

As the result of the analysis for Compound 002 by an elemental analyzer, the measured values of each element in the compound were C, 90.78%; H, 5.14%; N, 2.05%; Si, 2.03%; while the measured ones were C, 90.79%; H, 5.13%; N, 2.04%; Si, 2.04%.

Example 3

Synthesis of Compound 003-Silicon-Containing Bianthracene Derivate Containing Anthranyl Under a nitrogen environment, bis[10-(9-bromoanthranyl)]diphenyl silane (34.73 g, 50 mmol) and 10-(2-anthranyl)-9-anthranyl boronic acid (57.77 g, 135 mmol) were added into a three-necked flask equipped with a heating means, a refluxing means and a stirring means. Then potassium carbonate (17.97 g, 130 mmol), tetrahydrofuran (250 nil) and water (125 ml) were added. Thereafter, tetrakis(triphenylphosphine) palladium (0.81 g, 0.7 mmol) was added. The temperature was raised to 74° C., and the mixture was reacted for 26 hours while refluxing. The resultant mixture was cooled to room temperature, and after a solid was precipitated, vacuum filtration was carried out. After the resultant filter cake was washed with water, ethanol and diethyl ether in this order, it was purified by column chromatography (dichloromethane:petroleum ether=3:1). The solvent was recovered. After drying, an off-white Compound 003 (56.49 g) was obtained, and the yield thereof was 91% or more.

The specific synthesis route for Compound 003 was as follows:

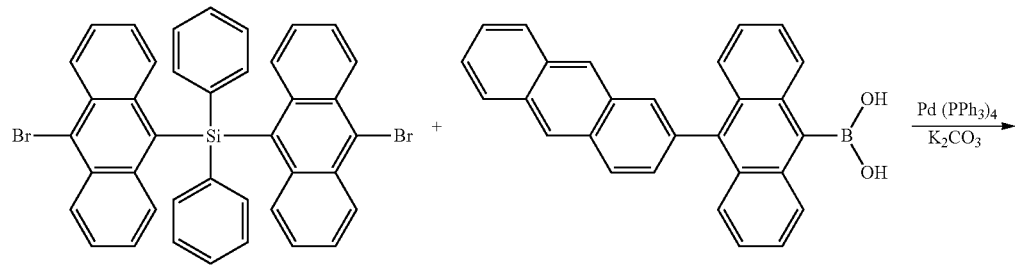

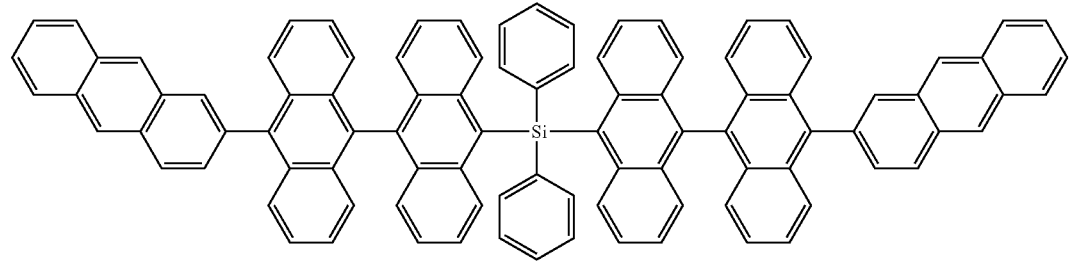

As the result of the analysis for Compound 003 by mass spectrography, the measured value of the molecular weight of the compound was 1241.58, while the calculated one was 1241.59.

As the result of the analysis for Compound 003 by an elemental analyzer, the measured values of each element in the compound were C, 92.86%; H, 4.89%; Si, 2.28%; while the calculated ones were C, 92.87%; H, 4.87%; Si, 2.26%.

Example 4

Synthesis of Compound 004-Silicon-Containing Bianthracene Derivate Containing Phenanthryl Under a nitrogen environment, bis[10-(9-bromoanthranyl)]diphenyl silane (34.73 g, 50 mmol) and 10-(2-phenanthryl)-9-anthranyl boronic acid (55.76 g, 140 mmol) were added into a three-necked flask equipped with a heating means, a refluxing means and a stirring means. Then potassium carbonate (20.73 g, 150 mmol), tetrahydrofuran (250 ml) and water (125 ml) were added. Thereafter, tetrakis(triphenylphosphine) palladium (0.92 g, 0.8 mmol) was added. The temperature was raised to 76° C., and the mixture was reacted for 27 hours while refluxing. The resultant mixture was cooled to room temperature, and after a solid was precipitated, vacuum filtration was carried out. After the resultant filter cake was washed with water, ethanol and diethyl ether in this order, it was purified by column chromatography (dichloromethane:petroleum ether=3:1). The solvent was recovered. After drying, an off-white Compound 004 (54.63 g) was obtained, and the yield thereof was 88% or more.

The specific synthesis route for Compound 004 was as follows:

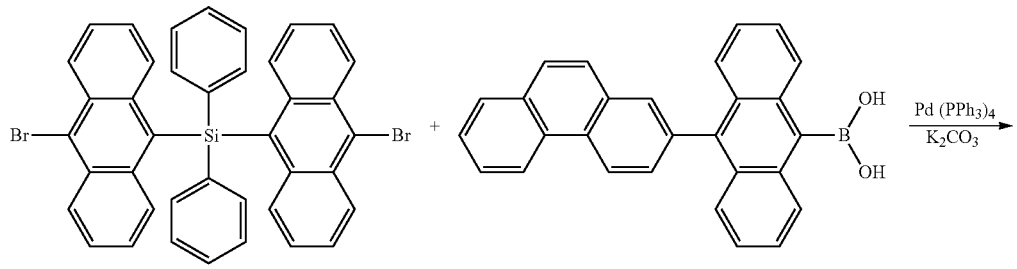

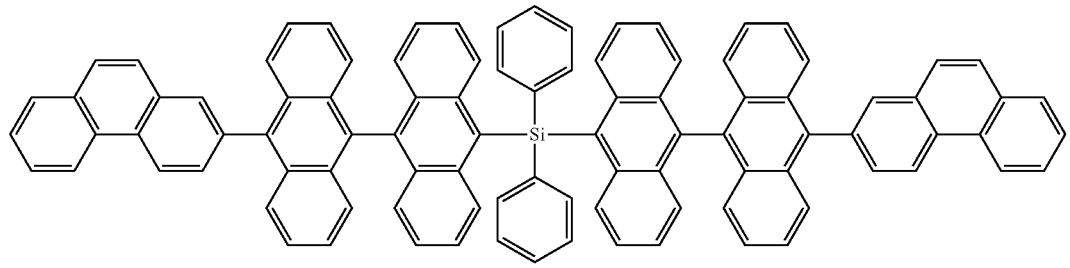

As the result of the analysis for Compound 004 by mass spectrography, the measured value of the molecular weight of the compound was 1241.57, while the calculated one was 1241.59.

As the result of the analysis for Compound 004 by an elemental analyzer, the measured values of each element in the compound were C, 92.86%; H, 4.89%; Si, 2.27%; while the calculated ones were C, 92.87%; H, 4.87%; Si, 2.26%.

Example 5

Synthesis of Compound 005-Silicon-Containing Bianthracene Derivate Containing Naphthyl Under a nitrogen environment, bis[10-(9-bromoanthranyl)]diphenyl silane (34.73 g, 50 mmol) and 10-(2-naphthyl)-9-anthranyl boronic acid 50.49 g, 145 mmol) were added into a three-necked flask equipped with a heating means, a refluxing means and a stirring means. Then potassium carbonate (24.19 g, 175 mmol), tetrahydrofuran (250 ml) and water (125 ml) were added. Thereafter, tetrakis(triphenylphosphine) palladium (1.04 g, 0.9 mmol) was added. The temperature was raised to 78° C., and the mixture was reacted for 28 hours while refluxing. The resultant mixture was cooled to room temperature, and after a solid was precipitated, vacuum filtration was carried out. After the resultant filter cake was washed with water, ethanol and diethyl ether in this order, it was purified by column chromatography (dichloromethane: petroleum ether=3:1). The solvent was recovered. After drying, an off-white Compound 005 (51.37 g) was obtained, and the yield thereof was 90% or more.

The specific synthesis route for Compound 005 was as follows:

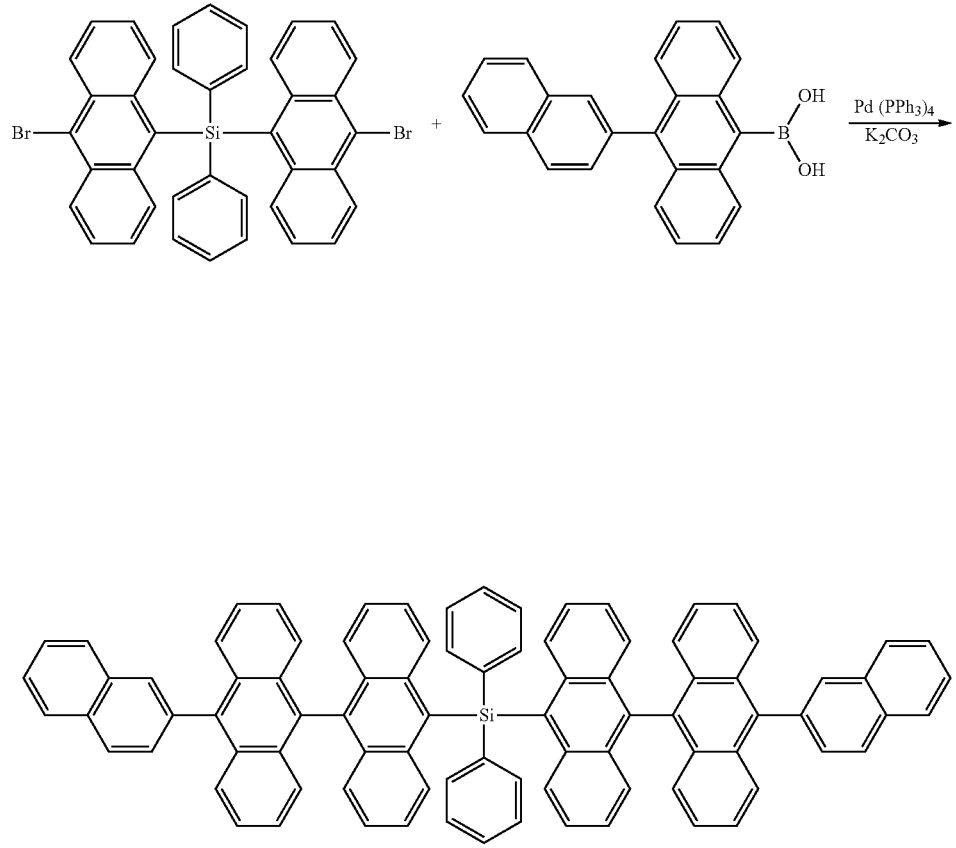

As the result of the analysis for Compound 005 by mass spectrography, the measured value of the molecular weight of the compound was 1141.45, while the calculated one was 1141.47.

As the result of the analysis for Compound 005 by an elemental analyzer, the measured values of each element in the compound were C, 92.57%; H, 4.95%; Si, 2.47%; while the calculated ones were C, 92.59%; H, 4.94%; Si, 2.46%.

Example 6

Synthesis of Compound 006-Silicon-Containing Bianthracene Derivate Containing 9,9-dimethyl-2-fluorenyl Under a nitrogen environment, bis[10-(9-bromoanthranyl)]diphenyl silane (34.73 g, 50 mmol) and 10-(9,9-dimethyl-2-fluorenyl)-9-anthranyl boronic acid (62.15 g, 150 mmol) were added into a three-necked flask equipped with a heating means, a refluxing means and a stirring means. Then potassium carbonate (27.64 g, 200 mmol), tetrahydrofuran (250 ml) and water (125 ml) were added. Thereafter, tetrakis (triphenylphosphine) palladium (1.16 g, 1.0 mmol) was added. The temperature was raised to 80° C., and the mixture was reacted for 30 hours while refluxing. The resultant mixture was cooled to room temperature, and after a solid was precipitated, vacuum filtration was carried out. After the resultant filter cake was washed with water, ethanol and diethyl ether in this order, it was purified by column chromatography (dichloromethane:petroleum ether=3:1). The solvent was recovered. After drying, an off-white Compound 006 (56.68 g) was obtained, and the yield thereof was 89% or more.

The specific synthesis route for Compound 006 was as follows:

Tests for Performances (1) Test for Purity

The Compounds 001-006 were subjected to the test for purity by high performance liquid chromatography (HLPC). The results are listed in Table 1.

(2) Test for Luminescence Efficiency

The samples were formulated into diluted solutions having a concentration of $1\times10^{-6}$ mol/L, respectively. The solutions were made into thin films via spin coating method and the luminescence efficiencies of the above-mentioned diluted solutions and thin films were measured respectively by Edinburdh-FLS920 (steady state/transient state fluorescence spectrometer). The specific data are shown in table 1.

TABLE 1

| Luminescence Efficiencies of the Compounds 001-006 obtained in the Examples | | | |
| --- | --- | --- | --- |
| Sample | Luminescence Efficiency in Diluted Solution | Luminescence Efficiency in Thin Film | HLPC Purity |
| Compound 001 | 94% | 80.1% | >98% |
| Compound 002 | 95% | 81.3% | >98% |
| Compound 003 | 96% | 82.4% | >98% |
| Compound 004 | 97% | 80.6% | >98% |
| Compound 005 | 98% | 89.3% | >98% |
| Compound 006 | 95% | 80.6% | >98% |

In the research for the synthesis of organic electroluminescent materials in prior art, the reports on the prior art of silicon compounds containing aryl group are relatively all-around. The luminescence efficiency of such silicon compound containing aryl group in a diluted solution can reach 81.8% at most, and that in a thin film ranges generally from 29%-89%.

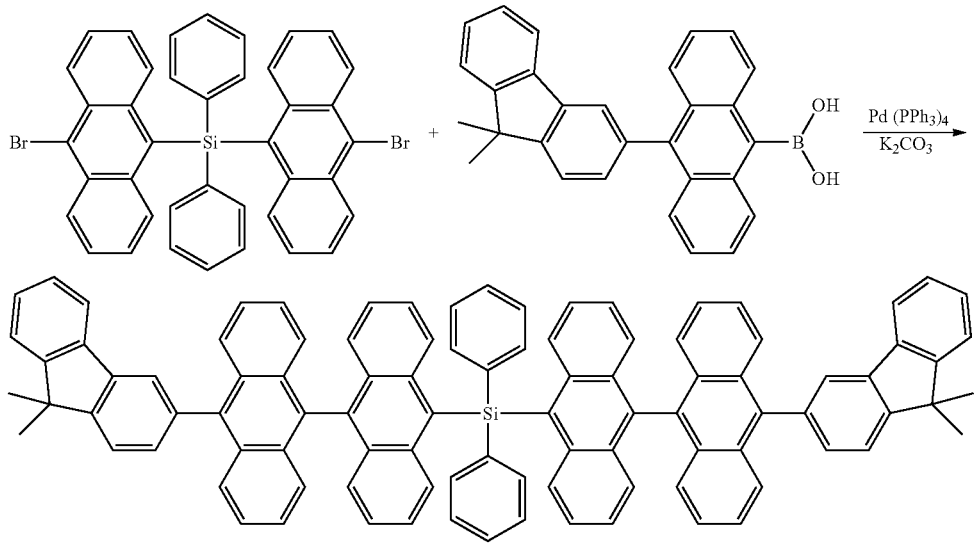

As the result of the analysis for Compound 006 by mass spectrography, the measured value of the molecular weight of the compound was 1273.65, while the calculated one was 1273.67.

As the result of the analysis for Compound 006 by an elemental analyzer, the measured values of each element in the compound were C, 92.43%; H, 5.37%; Si, 2.20%; while the calculated ones were C, 92.41%; H, 5.38%; Si, 2.21%.

However, the silicon-containing bianthracene derivate provided by the invention has a higher luminescence efficiency. As shown in table 1, each of the silicon-containing bianthracene derivates in Examples 1-6 has a luminescence efficiency in diluted solution of 94% or more, which is much higher than 81.8% in prior art. Each luminescence efficiency in thin film is 80% or more and can reach 89.3% at most. The high luminescence efficiency indicates that the silicon-containing bianthracene derivate absolutely can be used in an electroluminescent device as a luminescent material, a luminescent host material, and a transporting material.

Obviously, the above-mentioned Examples are merely examples provided for a clear illustration, and not the limitation of the embodiments. Changes or modifications in other different forms can be made by those skilled in the art on the basis of the previous description. It is unnecessary and impossible to list all of the embodiments one by one herein. The changes and modification derived herefrom are still in the protection scope of the invention.

What is claimed is:

1. A silicon-containing bianthracene derivative having a molecular structure of the following general formula:

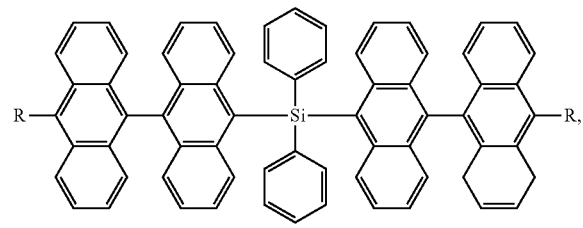

wherein R group represents an aryl group having a carbon atom number of 6-14, an aromatic heterocyclic group having a carbon atom number of 8-18, a fused-ring aromatic group having a carbon atom number of 9-15, a fluorenyl group, or a triarylamino group.

2. The silicon-containing bianthracene derivative according to claim 1, wherein the R group is one selected from N-phenyl-3-carbazyl, triphenylamino, 2-anthranyl, 2-phenanthryl, 2-naphthyl and 9,9-dimethyl-2-fluorenyl.

3. A production process for the silicon-containing bianthracene derivative according to claim 1, comprising the following steps of:
Step S1: adding bis[10-(9-bromoanthranyl)]diphenyl silane and an anthranyl boronic acid para-substituted by the R group into a reaction vessel;
Step S2: adding potassium carbonate and a solvent;
Step S3: adding a catalyst;
Step S4: raising the reaction temperature and performing refluxing, performing a reaction sufficiently to obtain the silicon-containing bianthracene derivative.

4. The production process according to claim 3, wherein the bis[10-(9-bromoanthranyl)]diphenyl silane in Step S1 is prepared from 9,10-dibromoanthracene and diphenyl dichlorosilane.

5. The production process according to claim 4, wherein the production process for the bis[10-(9-bromoanthranyl)]diphenyl silane in the Step S1 comprises the following steps of:
Step N1: adding 9,10-dibromoanthracene as a reactant to anhydrous tetrahydrofuran as a solvent;
Step N2: adding a solution of n-butyl lithium dropwise;
Step N3: stirring at room temperature, and cooling;
Step N4: adding diphenyl dichlorosilane, performing heating gradually to room temperature, stirring and cooling;
Step N5: obtaining the bis[10-(9-bromoanthranyl)]diphenyl silane, which can be directly used in Step S1, through extraction, washing, drying overnight, purification by column chromatography, and recrystallization.

6. The production process according to claim 5, wherein n-butyl lithium and 9,10-dibromoanthracene in the Step N2 have the following parts by mole of:
n-butyl lithium: 1-1.2 parts;
9,10-dibromoanthracene: 1 part.

7. The production process according to claim 5, wherein diphenyl dichlorosilane and 9,10-dibromoanthracene in the Step N4 have the following parts by mole of:
diphenyl dichlorosilane: 1 part;
9,10-dibromoanthracene: 3-4 parts.

8. The production process according to claim 5, wherein the solvent in the purification by column chromatography in the Step N5 is a mixed solvent of n-hexane and chloroform at a volume ratio of 1:4.

9. The production process according to claim 3, wherein bis[10-(9-bromoanthranyl)]diphenyl silane and the anthranyl boronic acid para-substituted by the R group in the Step S1 respectively have the following parts by mole of:
bis[10-(9-bromoanthranyl)]diphenyl silane: 1 part;
the anthranyl boronic acid para-substituted by the R group: 2.5-3 parts.

10. The production process according to claim 3, wherein potassium carbonate and bis[10-(9-bromoanthranyl)]diphenyl silane in the Step S2 respectively have the following parts by mole of:
potassium carbonate: 3-4 parts;
bis[10-(9-bromoanthranyl)]diphenyl silane: 1 part.

11. The production process according to claim 3, wherein the solvent in the Step S2 is a mixed solvent of tetrahydrofuran and water at a volume ratio of 2:1.

12. The production process according to claim 3, wherein the catalyst and bis[10-(9-bromoanthranyl)]diphenyl silane in the Step S3 have the following parts by mole of:
the catalyst: 1 part;
bis[10-(9-bromoanthranyl)]diphenyl silane: 50-100 parts.

13. The production process according to claim 3, wherein in the Step S4, the reaction temperature is 70-80° C., and the reflux reaction time is 24-30 hours.

14. An organic electroluminescent device comprising the silicon-containing bianthracene derivative according to claim 1 as an organic luminescent material, a luminescent host material, or a transporting material.

15. The organic electroluminescent device according to claim 14, wherein the R group is one selected from N-phenyl-3-carbazyl, triphenylamino, 2-anthranyl, 2-phenanthryl, 2-naphthyl, and 9,9-dimethyl-2-fluorenyl.

* * * * *